US005843852A

United States Patent [19]
Dutkiewicz et al.

[11] Patent Number: 5,843,852
[45] Date of Patent: Dec. 1, 1998

[54] ABSORBENT STRUCTURE FOR LIQUID DISTRIBUTION

[75] Inventors: Jacek Dutkiewicz, Appleton; Kristin Ann Goerg-Wood, Sherwood; Krzysztof Andrezej Szymonski, Neenah, all of Wis.; Lawrence Howell Sawyer, Roswell, Ga.; Connie Lynn Hetzler, Alpharetta, Ga.; Andrew S. Burnes, Lawrenceville, Ga.

[73] Assignee: Kimberly-Clark Worldwide, Inc., Neenah, Wis.

[21] Appl. No.: 767,645

[22] Filed: Dec. 17, 1996

[51] Int. Cl.⁶ ..................................................... B32B 5/06
[52] U.S. Cl. ..................... 442/334; 442/352; 604/358; 604/367; 604/374; 604/378
[58] Field of Search ................................. 442/334, 352; 604/367, 358, 374, 378; 162/157.6, 158, 182

[56] References Cited

U.S. PATENT DOCUMENTS

| | | | |
|---|---|---|---|
| 3,224,926 | 12/1965 | Bernardin | 162/146 |
| 3,339,550 | 9/1967 | Van Haaften | 128/290 |
| 3,434,918 | 3/1969 | Bernardin | 162/111 |
| 3,455,778 | 7/1969 | Bernardin | 162/113 |
| 4,822,453 | 4/1989 | Dean et al. | 162/157.6 |
| 4,888,093 | 12/1989 | Dean et al. | 162/157.6 |
| 4,889,595 | 12/1989 | Herron et al. | 162/157.6 |
| 4,889,596 | 12/1989 | Schoggen et al. | 162/157.6 |
| 4,898,642 | 2/1990 | Moore et al. | 162/157.6 |
| 4,935,022 | 6/1990 | Lash et al. | 604/368 |
| 4,989,642 | 2/1991 | Perry et al. | 137/625.37 |
| 4,994,037 | 2/1991 | Bernardin | 604/368 |
| 5,137,537 | 8/1992 | Herron et al. | 8/120 |
| 5,147,345 | 9/1992 | Young et al. | 604/378 |
| 5,183,707 | 2/1993 | Herron et al. | 428/364 |
| 5,217,445 | 6/1993 | Young et al. | 604/381 |
| 5,318,554 | 6/1994 | Young et al. | 604/378 |
| 5,348,547 | 9/1994 | Payne et al. | 604/378 |
| 5,350,370 | 9/1994 | Jackson et al. | 604/367 |
| 5,360,420 | 11/1994 | Cook et al. | 604/378 |
| 5,522,967 | 6/1996 | Shet | 162/9 |

FOREIGN PATENT DOCUMENTS

| | | | |
|---|---|---|---|
| 0 399 564 A3 | 11/1990 | European Pat. Off. | A61L 15/00 |
| 0 410 480 A2 | 1/1991 | European Pat. Off. | A61L 15/28 |
| 0 540 041 A1 | 5/1993 | European Pat. Off. | A61L 15/60 |
| 0 618 329 A1 | 10/1994 | European Pat. Off. | D21H 27/30 |
| 2 272 459 | 5/1994 | United Kingdom | A61F 13/15 |
| WO 94/10953 A1 | 5/1994 | WIPO | A61F 13/15 |
| WO 94/10954 A1 | 5/1994 | WIPO | A61F 13/15 |
| WO 94/10955 A1 | 5/1994 | WIPO | A61F 13/15 |
| WO 94/10956 A1 | 5/1994 | WIPO | A61F 13/15 |
| WO 94/10957 A1 | 5/1994 | WIPO | A61F 13/15 |

Primary Examiner—James J. Bell
Attorney, Agent, or Firm—John R. Schenian

[57] ABSTRACT

Disclosed is an absorbent structure comprising fibers, wherein the absorbent structure exhibits desired liquid transport properties. In one embodiment of the present invention, an absorbent structure comprises wettable cellulosic fibers, wherein the absorbent structure exhibits a Vertical Liquid Flux rate value at a height of about 15 centimeters of at least about 0.002 grams of liquid per minute per gram per square meter of absorbent structure per inch of cross-sectional width of the absorbent structure (g/(min*gsm*inch). The absorbent structure is suitable for use in disposable absorbent products.

26 Claims, No Drawings

ABSORBENT STRUCTURE FOR LIQUID DISTRIBUTION

BACKGROUND OF THE INVENTION

1. Field of the Invention

The present invention relates to an absorbent structure suitable for use in disposable absorbent products. More particularly, the present invention relates to an absorbent structure comprising wettable fibers, wherein the absorbent structure exhibits desired liquid transport properties.

2. Description of the Related Art

The purpose of disposable absorbent products is typically body waste management. In order to manage liquid body waste, the absorbent structure or structures within an absorbent product must generally be able to first uptake a liquid into the absorbent product, then distribute the liquid within the absorbent product, and then retain the liquid within the absorbent product.

In general, an absorbent product is insulted with a liquid in a relatively centralized location. In order to prevent leaks caused by the presence of more liquid than absorbent capacity in the centralized insult location, there is a need for the absorbent structure to transport the liquid away from the centralized insult location to more distant locations in the absorbent product.

If the distribution of the liquid by an absorbent structure within the absorbent product is not adequate, the efficiency of the absorbent structure's utilization of its capacity will be low. Typically, commercially available absorbent products are designed with an excess absolute liquid saturated retention capacity. Thus, the total absorbent capacity of the absorbent product is often not fully utilized. An increase in liquid distribution efficiency by the absorbent structure would potentially allow either a higher realized liquid saturation level for an absorbent product using the same amount of absorbent structure or the use of less absolute capacity to achieve the same realized liquid saturation level in the absorbent product without any increase in liquid leakage. The use of less absorbent structure to achieve the same realized liquid saturation level in an absorbent product will typically result in less absorbent product being disposed of to the environment.

It is therefore desirable to produce an absorbent structure able to exceed the liquid transport properties of known absorbent structures. It is also desirable to produce an absorbent structure that is capable of quickly transporting liquid from a centralized insult location to desired, more distant locations within the absorbent product. In one embodiment, it is also desirable to produce an absorbent structure that is prepared using natural fibers, due to cost and environmental concerns.

SUMMARY OF THE INVENTION

In one aspect, the present invention concerns an absorbent structure comprising fibers, wherein the absorbent structure exhibits desired liquid transport properties.

In one embodiment of the present invention, an absorbent structure comprises fibers, wherein the absorbent structure exhibits a Vertical Liquid Flux rate value at a height of about 15 centimeters of at least about 0.002 grams of liquid per minute per gram per square meter of absorbent structure per inch of cross-sectional width of the absorbent structure (g/(min*gsm*inch).

In another embodiment of the present invention, an absorbent structure comprises wettable cellulosic fibers, wherein the cellulosic fibers exhibit a Wet Curl value between about 0.11 and about 0.25.

In another aspect, it is desirable to provide a thin, disposable absorbent product, such as an infant diaper, which product employs an absorbent structure having a relatively small volume. Further, it is desirable to provide a disposable absorbent product which has a relatively small volume and a relatively high capacity.

In one embodiment, these goals are achieved in a disposable absorbent product comprising a liquid-permeable topsheet, a backsheet attached to the topsheet, and an absorbent structure positioned between the topsheet and the backsheet, wherein the absorbent structure comprises fibers and exhibits a Vertical Liquid Flux rate value at a height of about 15 centimeters of at least about 0.002 grams of liquid per minute per gram per square meter of absorbent structure per inch of cross-sectional width of the absorbent structure (g/(min*gsm*inch).

DETAILED DESCRIPTION OF THE INVENTION

One aspect of the present invention concerns an absorbent structure comprising fibers wherein the absorbent structure exhibits desired liquid transport properties.

As used herein, the term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

A wide variety of fibers can be employed in the preparation of the absorbent structure of the present invention. Illustrative fibers include, but are not limited to, cellulosic fibers such as wood and wood products, such as wood pulp fibers; non-woody paper-making fibers from cotton, from straws and grasses, such as rice and esparto, from canes and reeds, such as bagasse, from bamboos, from stalks with bast fibers, such as jute, flax, kenaf, cannabis, linen and ramie, and from leaf fibers, such as abaca and sisal; and man-made fibers obtained from regenerated cellulose or cellulose derivatives, such as cellulose acetate. It is also possible to use mixtures of one or more cellulosic fibers.

Other materials from which the absorbent structure may be made include synthetic fibers, woven fabrics and nonwoven webs. For example, the distribution layer may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The absorbent structure also can be a bonded carded web, an airlaid web or a wetlaid pulp structure composed of natural and/or synthetic fibers, or a combination thereof.

In one embodiment of the present invention, it is desirable that the fibers used to prepare an absorbent structure be wettable. As used herein, the term "wettable" is meant to refer to a fiber or material which exhibits a water in air contact angle of less than 90°. Suitably, the cellulosic fibers useful in the present invention exhibit a water in air contact angle between about 100 to about 500 and more suitably between about 20° to about 30°. Suitably, a wettable fiber refers to a fiber which exhibits a water in air contact angle of less than 90°, at a temperature between about 0° C. and about 100° C., and suitably at ambient conditions, such as about 23° C.

Suitable fibers are those which are naturally wettable. However, naturally nonwettable fibers can also be used. It is possible to treat the fiber surfaces by an appropriate method to render them more or less wettable. When surface treated fibers are employed, the surface treatment is desirably nonfugitive; that is, the surface treatment desirably does not wash off the surface of the fiber with the first liquid insult or contact. For the purposes of this application, a surface treatment on a generally nonwettable fiber will be considered to be nonfugitive when a majority of the fibers demonstrate a water in air contact angle of less than 90° for three consecutive contact angle measurements, with drying between each measurement. That is, the same fiber is subjected to three separate contact angle determinations and, if all three of the contact angle determinations indicate a contact angle of water in air of less than 90°, the surface treatment on the fiber will be considered to be nonfugitive. If the surface treatment is fugitive, the surface treatment will tend to wash off of the fiber during the first contact angle measurement, thus exposing the nonwettable surface of the underlying fiber, and will demonstrate subsequent contact angle measurements greater than 90°. Beneficial wettability agents include polyalkylene glycols, such as polyethylene glycols. The wettability agent is used in an amount comprising beneficially less than about 5 weight percent, suitably less than about 3 weight percent, and more suitably less than about 2 weight percent, of the total weight of the fiber, material, or absorbent structure being treated.

The fibers are present in the absorbent structure of the present invention in an amount effective to result in the absorbent structure being able to transport a desired amount of liquid under desired conditions. The fibers are beneficially present in the absorbent structure of the present invention in an amount of from about 50 to about 100 weight percent, suitably from about 70 to about 100 weight percent, and more suitably from about 80 to about 100 weight percent, based on the total weight of the absorbent structure.

During processing or preparation, a cellulosic fiber often has a curl imparted to it such that the fiber is no longer straight and becomes shortened. Such a curl may be the result of either chemical or mechanical means. The curl of a fiber may be quantified by a curl value which measures the fractional shortening of a fiber due to kink, twists, and/or bends in the fiber. For the purposes of this invention, a fiber's curl value is measured in terms of a two dimensional plane, determined by viewing the fiber in a two dimensional plane. To determine the curl value of a fiber, the projected length of a fiber as the longest dimension of a two dimensional rectangle encompassing the fiber, I, and the actual length of the fiber, L, are both measured. An image analysis method may be used to measure L and I. A suitable image analysis method is described in U.S. Pat. No. 4,898,642, incorporated herein in its entirety by reference. The curl value of a fiber can then be calculated from the following equation:

$$\text{Curl Value} = (L/I) - 1$$

Depending on the nature of the curl of a cellulosic fiber, such curl may be stable when the cellulosic fiber is dry but may be unstable when the cellulosic fiber is wet. The cellulosic fibers useful in preparing the absorbent structures of the present invention have been found to exhibit a substantially stable fiber curl when wet. This property of the cellulosic fibers may be quantified by a Wet Curl value, as measured according to the test method described herein, which is a length weighted mean curl average of a designated number of fibers, such as about 4000, from a fiber sample. As such, the Wet Curl value is the summation of the individual wet curl values for each fiber multiplied by the fiber's actual length, L, divided by the summation of the actual lengths of the fibers. It is hereby noted that the Wet Curl value, as determined herein, is calculated by only using the necessary values for those fibers with a length of greater than about 0.4 millimeter.

In general, the cellulosic fibers useful in preparing the absorbent structures of the present invention have been found to exhibit a Wet Curl value suitably between about 0.11 to about 0.25, more suitably between about 0.13 to about 0.22, and most suitably between about 0.15 to about 0.20. Cellulosic fibers exhibiting a suitable Wet Curl value have been found to generally result in an absorbent structure exhibiting the desired liquid transport properties described herein. In contrast, cellulosic fibers not exhibiting a suitable Wet Curl value have been found to generally not result in an absorbent structure exhibiting the desired liquid transport properties described herein. As such, the Wet Curl value of a cellulosic fiber may be used to conveniently determine if the cellulosic fiber will be capable of being used to prepare an absorbent structure that will exhibit the desired liquid transport properties described herein. If a mixture of two or more cellulosic fibers is used to prepare the absorbent structure of the present invention, the mixture of fibers should exhibit a Wet Curl value suitably between about 0.11 to about 0.25, more suitably between about 0.13 to about 0.22, and most suitably between about 0.15 to about 0.20.

In general, stiffer fibers preserve their shape, including curl, better in water than fibers which are not stiff. As such, stiffer fibers generally better maintain the porosity of an absorbent structure when wet thus making the wet absorbent structure more permeable to liquid. In addition, resiliency of the fibers is also an advantage if, for example, the absorbent structure is exposed to any stresses. Resiliency of a fiber will help the fiber to recover its original shape and, thus, the porous structure of the absorbent structure when the stress is removed. Again, this is advantageous for maintaining the liquid transport properties of the absorbent structure. The stiffness and resiliency of fibers can generally be improved by a variety of methods including crosslinking the fibers, such as with oxidation, sulfonation, heat-treatment, chemical crosslinkers, or by sizing the fibers with polymers such as starch or chitosan; changing the supermolecular structure of the fiber, such as by treating the fiber with swelling agents, such as alkaline solutions, and subsequently deswelling the fiber; and fractionating the source of the fibers so as to obtain pulp containing, for example, a higher amount of coarser, stiffer fibers, such as latewood fibers from wood sources.

In one embodiment of the present invention, a source of fibers is fractionated so as to obtain fibers that exhibit desired properties. Such a fractionation of fibers is disclosed in a patent application filed concurrently with the filing of this original patent application, wherein such patent application is entitled "Fractionation of Cellulosic Fibers", by Jacek Dutkiewicz et al., Ser. No. (Unknown), the disclosure of which is incorporated herein in its entirety by reference.

In general, a stiffer fiber may require less curl to be useful in the present invention. For example, coarse latewood fibers often have a relatively low Wet Curl value. Yet, an absorbent structure prepared, for example, from a latewood-rich fraction from a softwood kraft may possess effective porosity, permeability, and density to exhibit desired Vertical Liquid Flux rate values as described herein.

The presence of very small fibers, or fines, in the cellulosic fibers useful in preparing the absorbent structure of the present invention have been found to generally exhibit a negative effect on the liquid transport performance of the absorbent structure. As used herein, the term "fines" is intended to refer to very small fibers that have a length that is less than about 0.2 millimeter. The weight percent of fines in a fiber sample may be determined, for example, by using a fiber analyzer instrument, such as the Fiber Quality Analyzer, OpTest Product Code DA93, available from OpTest Equipment Inc., Ontario, Canada, the same equipment used herein to measure the Wet Curl value of a fiber sample. It is believed that such fines decrease the porosity of the absorbent structure and thus retard the transport of liquid. As such, it is desired that the amount of fines present in an absorbent structure of the present invention be minimized as much as possible. Desirably, the weight percent of fines in a fiber sample is less then about 4, suitably less than about 2, and more suitably less than about 1 weight percent of the total weight of fibers in the fiber sample.

The cellulose fibers useful in preparing the absorbent structure of the present invention may generally be prepared by a variety of methods, including mechanical, chemical, and thermal processes and combinations thereof. Such methods are suitable as long as such methods result in the cellulose fibers exhibiting the properties described herein so that the absorbent structure prepared using such fibers exhibits the desired liquid transport properties described herein.

One method of preparing the cellulose fibers useful in the present invention is to sulfonate the fibers. Such a process is generally described in U.S. Pat. No. 5,522,967, issued Jun. 4, 1996, by R. Shet, the disclosure of which is hereby incorporated herein in its entirety by reference.

Another method of preparing the cellulose fibers useful in the present invention is to heat treat the fibers. Such a process is generally described in a patent application filed concurrently with the filing of this original patent application, wherein such patent application is entitled "Treatment Process For Cellulosic Fibers", by Jacek Dutkiewicz et al., Ser. No. (Unknown), the disclosure of which is incorporated herein in its entirety by reference.

Another method of preparing the cellulose fibers useful in the present invention is to treat the cellulose fibers with a basic solution in order to swell the cellulose fibers. Such a process is generally described in copending patent application entitled "Treatment Process For Cellulosic Fibers", by Tong Sun et al., Ser. No. 60/029,343, filed Oct. 31, 1996, the disclosure of which is incorporated herein in its entirety by reference.

The basic solution may be prepared using an alkali metal hydroxide material, such as sodium hydroxide. In general, any combination of treatment in a basic solution and time which is effective in preparing the fibers, without undesirable damage to the fibers, so that an absorbent structure prepared from the basic-treated fibers exhibits the desired liquid transport properties described herein, is suitable for use in the present invention. As a general rule, the cellulose fibers will first be added to a basic solution, allowed to soak for a desired amount of time, and then neutralized with an acid solution to a pH of about 7. The treated cellulosic fibers may then be used to prepare an absorbent structure.

If sodium hydroxide is used to prepare the basic solution used to treat the cellulosic fibers, the basic solution beneficially has a concentration of from about 50 to about 500 grams of sodium hydroxide per liter of water and suitably from about 100 to about 300 grams of sodium hydroxide per liter of water. The treatment time of the cellulose fibers is beneficially from about 1 to about 10 minutes.

It has also been discovered that, by using a steam explosion process for treating cellulosic fibers, and by using appropriate treatment conditions, modified cellulosic fibers exhibiting desired properties may be prepared by an efficient and effective process. Such a process is generally described in a patent application filed concurrently with the filing of this original patent application, wherein such patent application is entitled "Treatment Process For Cellulosic Fibers", by Sheng-Hsin Hu, Ser. No. (Unknown), the disclosure of which is incorporated herein in its entirety by reference.

Other methods of preparing the cellulose fibers for use in an absorbent structure of the present invention include oxidizing the cellulose. In addition, cellulose fibers prepared from one of the above-described methods may be mixed together with non-treated cellulose fibers, with cellulose fibers prepared from another one of the above-described methods, or other non-cellulosic fibers to form a blend of fibers that is useful in preparing the absorbent structure of the present invention.

In general, it is desired that the absorbent structure of the present invention can quickly and effectively transport liquid from a centralized liquid insult location to distant locations within the absorbent structure or within a disposable absorbent product. With such an ability, the absorbent structure of the present invention will be useful, for example, as a liquid distribution material within a disposable absorbent product. Distribution must take place at an acceptable speed such that the target insult area, generally the crotch area, is ready for the next insult. The time between insults can range from just a few minutes to hours, generally depending on the age of the wearer. In order to achieve this transportation function, a distribution layer must have a high capillary tension value. Capillary tension in distribution and other materials not containing superabsorbents is measured simply by the equilibrium vertical wicking height of a 8.5 g/l saline solution, not by the test method given for materials containing superabsorbents. A successful distribution layer must have a capillary tension greater than the adjacent material from which it receives liquid (on the side toward the wearer) and preferably a capillary tension of at least about 15 cm. Because of the generally inverse relationship between capillary tension and permeability, such a high capillary tension indicates that the distribution layer will usually have a low permeability.

In the case of an infant's diaper, for example, it is desired that about 8 grams of a distribution material having a basis weight of about 200 grams per square meter would be capable of being able to transport about 100 milliliters of liquid, and suitably about 120 milliliters of liquid, within about 30 minutes to a distance of up to about 15 centimeters away from a centralized liquid insult location.

One liquid transport property desired of the absorbent structure of the present invention is that the absorbent structure exhibits a Vertical Liquid Flux rate, at a height of about 15 centimeters, suitably of at least about 0.002 grams of liquid per minute per gram per square meter of absorbent structure (gsm) per inch of cross-sectional width of the absorbent structure (g/(min*gsm*inch), more suitably of at least about 0.0025 g/(min*gsm*inch), most suitably of at least about 0.003 g/(min*gsm*inch), and up to about 0.1 g/(min*gsm*inch). As used herein, the Vertical Liquid Flux rate value of an absorbent structure is meant to represent the amount of liquid transported across a boundary a specified vertical distance away from a centralized liquid insult location per minute per normalized quantity of the absorbent structure. The Vertical Liquid Flux rate, at a height of about 15 centimeters, of an absorbent structure may be measured according to the test method described herein.

Another liquid transport property desired of the absorbent structure of the present invention is that the absorbent structure exhibits a Vertical Liquid Flux rate, at a height of about 5 centimeters, suitably of at least about 0.01 g/(min*gsm*inch), more suitably of at least about 0.015 g/(min*gsm*inch), most suitably of at least about 0.02 g/(min*gsm*inch), and up to about 0.5 g/(min*gsm*inch). The Vertical Liquid Flux rate, at a height of about 5 centimeters, of an absorbent structure may be measured according to the test method described herein.

Another liquid transport property desired of the absorbent structure of the present invention is that the absorbent structure exhibits a Wicking Time value of a liquid to an elevation of 15 centimeters of suitably less than about 3.5 minutes, more suitably less than about 3 minutes, and most suitably less than about 2.5 minutes. As used herein, the Wicking Time value of an absorbent structure is meant to represent the time needed to transport a liquid a specified vertical distance away from a centralized liquid insult location. The Wicking Time value of a liquid to an elevation of 15 centimeters for an absorbent structure may be measured according to the test method described herein.

The absorbent structure of the present invention should have a density such that the absorbent structure exhibits the desired liquid transport properties described herein. The density of an absorbent structure generally determines the porosity, permeability, and capillary structure of the absorbent structure. If the density of the absorbent structure is too high, the capillaries of the absorbent structure will generally be too small such that the capillaries provide a relatively high capillary tension force but, because of the relatively small capillaries, the permeability of the absorbent structure will be relatively low. If the permeability of the absorbent structure is relatively low, the absorbent structure will generally only transport relatively small amounts of liquid so that the vertical liquid flux rate of the absorbent structure will be relatively low at, for example, each of about 5 centimeters and of about 15 centimeters of height from a source of liquid.

Conversely, If the density of the absorbent structure is too low, the permeability of the absorbent structure will be relatively high. However, the capillaries of the absorbent structure will generally be relatively large such that the capillaries provide a relatively low capillary tension force that results in the absorbent structure being generally unable to quickly transport liquid to relatively high elevations such as about 15 centimeters of height from a source of liquid. Thus, such an absorbent structure may exhibit a relatively high vertical liquid flux rate at a height, for example, of about 5 centimeters of height from a source of liquid but the liquid will move slower and slower, or stop altogether, the higher the front of the wicked liquid. Thus, the vertical liquid flux rate of such an absorbent structure will be relatively low at, for example, about 15 centimeters of height from a source of liquid.

Depending on the stability of the capillary structure of an absorbent structure, the density of the absorbent structure may change as a liquid enters into the capillary structure of the absorbent structure. Generally, the structural stability of the absorbent structure will depend on such factors as the stability, as measured, for example, by shape, curl, stiffness, or resiliency, of the fibers in the absorbent structure as well as the stability of the absorbent structure as a whole. Structural changes of the absorbent structure are even more likely if the absorbent structure is under a stress or pressure as, for example, when the absorbent structure is used in a diaper being worn by a human. Thus, it is desirable that the density of the absorbent structure does not substantially change when the absorbent structure absorbs a liquid or otherwise becomes wet or is under a stress or pressure and/or that the absorbent structure substantially recovers its density after the liquid or stress or pressure is removed from the absorbent structure. The stability of the density of an absorbent structure may be quantified, for example, by the difference in densities exhibited by the absorbent structure when different loads, such as each of loads of about 0.15 pound per square inch and about 0.3 pound per square inch, are applied to the absorbent structure. If the difference in the densities exhibited by the absorbent structure at the different loads is relatively small, the absorbent structure may be considered to be structurally stable. Another method of characterizing the structure of an absorbent structure is by measuring the void volume of the absorbent structure. The absorbent structure may have a basis weight of from about 35 to about 300 gsm, or more preferably from about 80 to about 200 gsm, a density of between about 0.08 and about 0.5 g/cc and a permeability between about 50 and about 1000 Darcys.

It is generally desirable to use as little of an absorbent structure in a disposable absorbent product as is necessary to provide the desired liquid transportation properties. Thus, the absorbent structure of the present invention exhibits a total weight that is suitably less than 10 grams, more suitably less than about 8 grams, and most suitably less than about 7 grams.

The absorbent structure of the present invention should exhibit sufficient dry and wet tensile strengths such that the absorbent structure maintains its structural integrity during manufacturing, handling, and use. In general, the dry and wet tensile strengths typical of wet-laid absorbent structures should be suitable for an absorbent structure of the present invention. In general, it is desired that an absorbent structure of the present invention, having a basis weight of about 200 grams per square meter, exhibits a dry tensile strength that is beneficially at least about 5000 grams of force per inch of absorbent structure width, suitably at least about 7500 grams of force per inch of absorbent structure width, and more suitably at least about 10000 grams of force per inch of absorbent structure width. In general, it is desired that an absorbent structure of the present invention exhibits a wet tensile strength that is beneficially at least about 500 grams of force per inch of absorbent structure width, suitably at least about 1000 grams of force per inch of absorbent structure width, and more suitably at least about 2000 grams of force per inch of absorbent structure width.

If desired, a wet strength resin may be added to the fibers forming an absorbent structure to improve the wet strength properties of the absorbent structure. However, the wet strength resin should be sufficiently hydrophilic so that the resin does not adversely affect the wettability of the fibers.

Because it is desired that the absorbent structures of the present invention should exhibit sufficient dry and wet tensile strengths, it is generally desired that the process used to prepare the absorbent structure be a wet-laying process. This is because a wet laying process generally provides an absorbent structure which exhibits sufficient dry and wet tensile strengths. In contrast, an air-laying process generally results in an absorbent structure that will not exhibit sufficient dry and wet tensile strengths. However, by using wet strength resins, binder fibers, or by the careful selection of fibers used to prepare the absorbent structure, an air-laid absorbent structure can be prepared that exhibits the properties desired in the present invention. Binder fibers suitable for use in the present invention are well known and are described, for example, in copending patent application entitled "Absorbent Structure Comprising Superabsorbent, Staple Fiber, and Binder Fiber", Ser. No. 08/294,155, by Andrew E. Huntoon et al., filed Aug. 22, 1994, incorporated herein in its entirety by reference.

Suitably, the process used to prepare the absorbent structure is an uncreped, through-air dried (UCTAD) process. Such a process is described, for example, in pending U.S. patent application, Ser. No. 08/310,186, filed Sep. 21, 1994, by Fung-Jou Chen et al., incorporated herein in its entirety by reference.

It has also been discovered that the liquid transport properties of an absorbent structure of the present invention may be improved if the absorbent structure is a composite comprising multiple layers or sections of separate absorbent structures as compared to a unitary absorbent structure. As such, instead of preparing a unitary absorbent structure of a particular size or dimension, it may be desirable to prepare separate absorbent structure layers or sections that, when attached or combined with each other, form a composite that is substantially the same size and/or dimensions as the unitary absorbent structure. As an example, instead of preparing a unitary absorbent structure having a basis weight of about 200 grams per square meter, it may be desirable to prepare four separate absorbent structure layers each having a basis weight of about 50 grams per square meter. If effectively attached or combined with each other, the four smaller absorbent structure layers will form a composite that has a basis weight of about 200 grams per square meter and otherwise substantially has the same size and/or dimensions as the unitary absorbent structure.

In one embodiment of the present invention, a disposable absorbent product is provided, which disposable absorbent product comprises a liquid-permeable topsheet, a backsheet attached to the topsheet, and an absorbent structure positioned between the topsheet and the backsheet wherein the absorbent structure comprises wettable cellulosic fibers and wherein the absorbent structure exhibits desired liquid transport properties.

While one embodiment of the invention will be described in terms of the use of an absorbent structure in an infant diaper, it is to be understood that the absorbent structure is equally suited for use in other disposable absorbent products known to those skilled in the art such as training pants, feminine care products such as pads and tampons, incontinence products, and health care products such as capes or gowns.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

Disposable absorbent products, according to all aspects of the present invention, are generally subjected during use to multiple insults of a body liquid. Accordingly, the disposable absorbent products are desirably capable of absorbing multiple insults of body liquids in quantities to which the absorbent products and structures will be exposed during use. The insults are generally separated from one another by a period of time.

Test Methods

Wet Curl of Fibers

The Wet Curl value for fibers was determined by using an instrument which rapidly, accurately, and automatically determines the quality of fibers, the instrument being available from OpTest Equipment Inc., Hawkesbury, Ontario, Canada, under the designation Fiber Quality Analyzer, OpTest Product Code DA93.

A sample of fibers was obtained from the fiber pulp used to prepare the sample handsheet. The fiber sample was poured into a 600 milliliter plastic sample beaker to be used in the Fiber Quality Analyzer. The fiber sample in the beaker was diluted with tap water until the fiber concentration in the beaker was about 10 to about 25 fibers per second for evaluation by the Fiber Quality Analyzer.

An empty plastic sample beaker was filled with tap water and placed in the Fiber Quality Analyzer test chamber. The <System Check> button of the Fiber Quality Analyzer was then pushed. If the plastic sample beaker filled with tap water was properly placed in the test chamber, the <OK> button of the Fiber Quality Analyzer was then pushed. The Fiber Quality Analyzer then performs a self-test. If a warning was not displayed on the screen after the self-test, the machine was ready to test the fiber sample.

The plastic sample beaker filled with tap water was removed from the test chamber and replaced with the fiber sample beaker. The <Measure> button of the Fiber Quality Analyzer was then pushed. The <New Measurement> button of the Fiber Quality Analyzer was then pushed. An identification of the fiber sample was then typed into the Fiber Quality Analyzer. The <OK> button of the Fiber Quality Analyzer was then pushed. The <Options> button of the Fiber Quality Analyzer was then pushed. The fiber count was set at 4,000. The parameters of scaling of a graph to be printed out may be set automatically or to desired values. The <Previous> button of the Fiber Quality Analyzer was then pushed. The <Start> button of the Fiber Quality Analyzer was then pushed. If the fiber sample beaker was properly placed in the test chamber, the <OK> button of the Fiber Quality Analyzer was then pushed. The Fiber Quality Analyzer then began testing and displayed the fibers passing through the flow cell. The Fiber Quality Analyzer also displayed the fiber frequency passing through the flow cell, which should be about 10 to about 25 fibers per second. If the fiber frequency is outside of this range, the <Stop> button of the Fiber Quality Analyzer should be pushed and the fiber sample should be diluted or have more fibers added to bring the fiber frequency within the desired range. If the fiber frequency is sufficient, the Fiber Quality Analyzer tests the fiber sample until it has reached a count of 4000 fibers at which time the Fiber Quality Analyzer automatically stops. The <Results> button of the Fiber Quality Analyzer was then pushed. The Fiber Quality Analyzer calculates the Wet Curl value of the fiber sample, which prints out by pushing the <Done> button of the Fiber Quality Analyzer.

Water Retention

A 0.5 gram cellulosic fiber sample was obtained and dispersed into about 200 grams of deionized water using a Hobart Company Model N 50 blender set on the low speed setting for about 30 seconds. The cellulosic fiber/water solution was transferred to a beaker and allowed to sit for about 16 hours. The excess water was decanted and the cellulosic fibers were placed into a centrifuge (Dynac II by Clay Adams, Division of Becton Dickinson & Co., Model 5025, serial 012, cat. No. 0103) tube fitted with a screen. The cellulosic fibers were then centrifuged under a force of about 1000 time gravity for about 20 minutes. The cellulosic fibers were then removed from the centrifuge tube and weighed (giving a wet weight $W_w$). The cellulosic fibers were then dried at about 105° C. for about 2 hours. The cellulosic fibers were then reweighed (giving a dry weight $W_D$). The Water Retention value is then calculated by subtracting the dry weight ($W_D$) from the wet weight ($W_W$) and then dividing that value by the dry weight ($W_D$). The Water Retention value is reported as the grams of water retained per gram of dry cellulosic fibers.

Preparation of Wet-Laid Handsheet

A 17 inch by 17 inch standard handsheet having a basis weight of about 200 grams per square meter was prepared using a desired fiber sample by using a 16 inch by 16 inch cast bronze wet-laid handsheet former mold, available from Voith Corporation.

A British Disintegrator mixer, available from Testing Machines, Inc., was filled with about 2 liters of distilled water at room temperature (about 23° C.) and about 37.3 grams of the fiber sample. The counter on the British Disintegrator was set to zero and the cover was placed on the British Disintegrator. The British Disintegrator was turned on until the counter runs to about 600. Alternatively, the British Disintegrator may be run for about 5 minutes. A bucket was filled with about 8 liters of distilled water. The contents of the British Disintegrator was then also poured into the bucket.

The handsheet former, having an about 12 inch deep chamber, was filled with tap water to about 5 inches below the top of the handsheet former chamber. The contents of the bucket were then poured into the handsheet former chamber. A dedicated stirrer was then used to mix the suspension in the handsheet former chamber. The stirrer was moved slowly up and down 6 times to cause small vortexes, but to avoid causing large vortexes, in the square pattern of the handsheet former. The stirrer was then removed and the suspension was drained through the forming screen of the handsheet former. The handsheet former was then opened and two layers of blotting paper were placed on the top of the handsheet. A roller, having the equivalent of about 2.3 pounds of pressure per linear inch, was moved back and forth once on each of the left side, the right side, and the center of the formed handsheet. The blotting paper, with the formed handsheet attached, was then lifted off the forming screen. The blotting paper was then placed on a table such that the formed handsheet faced upwards. An 18 inch by 18 inch, 4 mesh nylon screen was placed on top of the handsheet. The blotting paper, handsheet, and screen were then flipped so that the screen was on the bottom and the blotting paper was on top. The blotting paper was then peeled off of the handsheet, leaving the handsheet on the screen. The edges of the handsheet were fastened to the screen using binder clips. The handsheet was left overnight to air-dry. The handsheet, attached to the screen, was then placed in an oven and dried at about 105° C. for about an hour. The handsheet was then removed from the oven and removed from the screen. The handsheet was then ready for evaluation for liquid distribution properties.

Bulk and Dry Density of an Absorbent Structure

From a handsheet prepared according to the procedure described herein, a strip of sample handsheet material, having a width of about 2 inches and a length of about 15 inches, was obtained by using a textile saw available, for example from Eastman, Machine Corp., Buffalo, N.Y. The sample strip was cut at least about 1 inch away from the edge of the handsheet so as to avoid edge effects. The sample strip was marked in about 10 millimeter intervals using water-soluble ink.

To measure the bulk of the sample strip, a bulk meter accurate to at least about 0.01 millimeter, such as a bulk meter available from Mitutoyo Corporation, was used. An about one inch diameter platen was used to measure the bulk, with the platen being parallel to the base of the bulk meter. The bulk of the sample strip was measured in about 50 millimeter intervals along the length of the sample strip and then averaged. The average bulk of the sample strip was then used to calculate the dry density of the sample strip, using the weight and dimensions of the sample strip. The wet density of the sample strip may be similarly determined after the sample strip has evaluated for Liquid Flux values.

Wicking Time and Vertical Liquid Flux of an Absorbent Structure

From a handsheet prepared according to the procedure described herein, a strip of sample handsheet material, having a width of about 2 inches and a length of about 15 inches, was obtained by using a textile saw available, for example from Eastman, Machine Corp., Buffalo, N.Y. The sample strip was cut at least about 1 inch away from the edge of the handsheet so as to avoid edge effects.

The apparatus used for holding a sample material while measuring the Wicking Time and Vertical Liquid Flux values for the sample material consists of male and female halves. The apparatus had a length of about 21 inches and consists of glued Plexiglas. Small nails are placed in the male bar about one inch apart. The female half has holes drilled to accommodate the nails. A 4 mesh nylon screen was stretched onto the nails. The screen was about one inch shorter than the sample holder at both ends. Reinforcing plates stiffened the bar, preventing the bar from buckling under the tension from the nylon screen. Short, flat, perpendicular bars act as springs to stretch the nylon screen and to keep the sample in place.

The sample strip was placed on the nylon screen, with the bottom end of the sample strip placed lower than the bottom edge of the sample holder such that when the sample strip is positioned on the top of the liquid distribution manifold at the beginning of the experiment, the bottom of the sample strip will just touch the liquid surface. A second 4 mesh nylon screen was stretched and placed on top of the sample strip. Two steel pins were driven through the sample strip at each of 5, 10, 15, and 30 centimeters from the bottom of the sample strip to prevent the movement of the sample strip under the weight of absorbed liquid. The female half of the sample holder was fitted onto the male half. Binder clips were used to keep the assembled holder together.

During the evaluation, the sample strip and the sample holder were contained in a Plexiglas tubular enclosure having an inner diameter of about 7.25 inches and a height of about 24 inches. There is a slit (about 0.25 inch by about 3 inches) in the bottom of the tubular enclosure large enough to allow the tube from the aspirator bottle to the liquid distribution manifold to go through. The tubular enclosure was covered with a flat piece of Plexiglas. Distilled water was sprayed on the walls of the tubular enclosure before the experiment to raise the relative humidity inside the tubular enclosure so as to reduce the evaporation of water from the sample strip during the evaluation. The relative humidity should be maintained at about 90 to about 98 relative humidity during the evaluation. The liquid distribution manifold and the tubular enclosure rest on the top of a Plexiglas plate resting on two lab jacks used for adjustability, stability, and maintaining level.

The aspirator bottle was filled with a 0.9 weight percent sodium chloride aqueous solution. The solution in the aspirator bottle was in equilibrium with the upper edge of the slit in the bottom of the tubular enclosure. The scale was tared. The sample holder was placed on the top of the liquid distribution manifold. A stopwatch was started as soon as the bottom edge of the sample strip touched the surface of the solution. The cover was placed on the top of the tubular enclosure.

The vertical distance of the liquid front traveling up the sample strip and the liquid weight absorbed by the sample strip at various times was recorded. The time versus liquid front height was plotted to determine the Wicking Time at about 5 centimeters and at about 15 centimeters. The weight of the liquid absorbed by the sample strip from the beginning of the evaluation to about 5 centimeters and to about 15 centimeters height was also determined from the data. The Vertical Liquid Flux value of the sample strip at a particular height was calculated by dividing the grams of liquid absorbed by the sample strip by each of: the basis weight, in grams per square meter, of the sample strip; the time, in minutes, needed by the liquid to reach the particular height; and the width, in inches, of the sample strip.

EXAMPLES

Example 1

Bleached southern softwood (pine) kraft pulp was made into wet-laid handsheets according to the procedure described in the Test Methods section herein.

Example 2

Bleached northern softwood (spruce) kraft pulp was made into wet-laid handsheets according to the procedure described in the Test Methods section herein.

Example 3

Northern Douglas fir pulp was made into wet-laid handsheets according to the procedure described in the Test Methods section herein.

Example 4

Pulp, available from Weyerhaeuser Company under the designation NHB416 pulp, was made into wet-laid handsheets according to the procedure described in the Test Methods section herein.

Example 5

Pulp, available from Buckeye Cellulose under the designation HPZ pulp, was made into wet-laid handsheets according to the procedure described in the Test Methods section herein.

Example 6

Bleached southern softwood (pine) kraft pulp was heat-treated in an oven at about 200° C. for about 20 minutes and was then made into wet-laid handsheets according to the procedure described in the Test Methods section herein.

Example 7

Bleached southern softwood (pine) kraft pulp was heat-treated in an oven at about 230° C. for about 5 minutes and was then made into wet-laid handsheets according to the procedure described in the Test Methods section herein.

Example 8

Bleached southern softwood (pine) kraft pulp was heat-treated in an oven at about 230° C. for about 5 minutes and was then made into wet-laid handsheets according to the following procedure:

The fibers were pulped at about 4 percent consistency in a hydropulper for about 30 minutes. The fibers were pumped into a stock chest and diluted to about 1.0 percent consistency. About 20 pounds per ton of Kymene 557 LX wet strength agent was added to the stock chest and allowed to mix for about 30 minutes. A single-layer, blended sheet of about 30 grams per square meter dry weight was formed on an Albany 94M forming fabric and dewatered with about 5 inches (about 127 millimeters) of mercury vacuum. The forming fabric was traveling at about 69 feet per minute (about 0.35 meters per second). The sheet was transferred at about a 15 percent rush transfer to a Lindsay 952-S05 transfer fabric traveling at about 60 feet per minute (about 0.30 meters per second). The vacuum in the transfer between the forming fabric and transfer fabric was about 10 inches (about 254 millimeters) of mercury. The sheet was vacuum transferred at about 12 inches (about 305 millimeters) of mercury to a throughdryer fabric, a Lindsay T116-1 fabric, traveling at about 60 feet per minute (about 0.30 meters per second), the same speed as the transfer fabric. The sheet and throughdryer fabric traveled over a fourth vacuum at about 12 inches (about 305 millimeters) of mercury just prior to entering a Honeycomb throughdryer operating at about 200° F. (about 93° C.) and dried to a final dryness of about 94–98 percent consistency. The sheets were aged for over 5 days at less than about 50 percent humidity at about 70° F. (about 21° C.).

Example 9

A mixture of cellulose fibers was prepared comprising about 60 weight percent of bleached southern softwood (pine) kraft pulp and about 40 weight percent of a pulp, available from Weyerhaeuser Company under the designation NHB416 pulp. The mixture was then made into wet-laid handsheets according to the procedure described in the Test Methods section herein.

Example 10

A mixture of cellulose fibers was prepared comprising about 60 weight percent of bleached southern softwood (pine) kraft pulp and about 40 weight percent of a pulp, available from Buckeye Cellulose under the designation HPZ pulp. The mixture was then made into wet-laid handsheets according to the procedure described in Example 8.

Example 11

Never-dried bleached southern softwood (pine) kraft pulp, having a consistency of about 35 weight percent, was soaked in a sodium hydroxide solution, having a concentration of about 200 grams of sodium hydroxide per liter of water, at about 25° C. for about 5 minutes. The resulting pulp was washed with water and neutralized with acetic acid to about pH 6.5 and was then made into wet-laid handsheets according to the procedure described in the Test Methods section herein.

Example 12

Never-dried bleached southern softwood (pine) kraft pulp, having a consistency of about 35 weight percent, was soaked in a sodium hydroxide solution, having a concentration of about 200 grams of sodium hydroxide per liter of water, at about 25° C. for about 5 minutes. The resulting pulp was washed with water and neutralized with acetic acid to about pH 6.5. A mixture of cellulose fibers was prepared comprising about 80 weight percent of the sodium hydroxide solution treated fibers and about 20 weight percent of untreated never-dried bleached southern softwood (pine)

kraft pulp. The mixture of cellulose fibers was then made into wet-laid handsheets according to the procedure described in the Test Methods section herein.

Example 13

Never-dried bleached southern softwood (pine) kraft pulp, having a consistency of about 35 weight percent, was soaked in a sodium hydroxide solution, having a concentration of about 200 grams of sodium hydroxide per liter of water, at about 25° C. for about 5 minutes. The resulting pulp was washed with water and neutralized with acetic acid to about pH 6.5. A mixture of cellulose fibers was prepared comprising about 50 weight percent of the sodium hydroxide solution treated fibers and about 50 weight percent of untreated never-dried bleached southern softwood (pine) kraft pulp. The mixture of cellulose fibers was then made into wet-laid handsheets according to the procedure described in the Test Methods section herein.

Example 14

Bleached southern softwood (pine) kraft pulp was soaked with an aqueous solution comprising about 0.1 weight percent phosphoric acid, heat-treated in an oven at about 150° C. for about 20 minutes, and was then made into wet-laid handsheets according to the procedure described in the Test Methods section herein.

Example 15

Sulfonated pulp was made into wet-laid handsheets according to the procedure described in Example 8.

Samples of the pulps used to prepare the handsheets were evaluated for Wet Curl values according to the Test Method described herein. The prepared handsheets were evaluated for basis weight, dry density, Vertical Liquid Flux (at each of 5 centimeters and 15 centimeters), and Wicking Time (at 15 centimeters) according to the Test Method described herein.

(available from Kimberly-Clark Corporation under the designation CR54 southern softwood kraft pulp) and about 5 weight percent of a 2.8 denier, 0.25 inch long bicomponent binder fiber with an activated copolyolefin sheath and a polyethyleneterephthlate core, available from Hoechst Celanese under the designation T255 binder fiber. The two fibrous components were intimately blended to form the base web which was bonded in a hot air oven with compaction in a smooth calender to a density of about 0.16 grams per cubic centimeter. The prepared absorbent structures exhibited a wicking time to a 15 centimeter vertical height of about 3 minutes and 20 seconds and Vertical Liquid Flux rate values of between about 0.0022 to about 0.0025 g/(min*gsm*inch).

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent structure comprising fibers, wherein the fibers exhibit a Wet Curl value that is between about 0.11 to about 0.25 and wherein the absorbent structure exhibits a Vertical Liquid Flux rate value at a height of about 15 centimeters of at least about 0.002 grams of liquid per minute per gram per square meter of absorbent structure per inch of cross-sectional width of the absorbent structure.

2. The absorbent structure of claim 1 wherein the fibers are cellulosic fibers.

3. The absorbent structure of claim 2 wherein the cellulosic fibers are wood pulp fibers.

4. The absorbent structure of claim 3 wherein the cellulosic fibers are wettable.

5. The absorbent structure of claim 4 wherein the wettable cellulosic fibers exhibit a Wet Curl value that is between about 0.11 to about 0.25.

TABLE 1

| Example | Wet Curl | Basis Weight (gsm) | Dry Density (g/cm³) | Vertical Liquid Flux at 5 cm (g/(min*gsm*inch)) | Vertical Liquid Flux at 15 cm (g/(min*gsm*inch)) | Wicking Time to 15 cm (min) |
|---|---|---|---|---|---|---|
| 1. | 0.09 | 210 | 0.19 | 0.007 | 0.0009 | 7.0 |
| 2. | 0.10 | 230 | 0.25 | 0.003 | 0.0005 | 10.7 |
| 3. | 0.10 | 240 | 0.26 | 0.005 | 0.00002 | 10.6 |
| 4. | 0.28 | 210 | 0.11 | 0.040 | 0.0015 | 3.8 |
| 5. | 0.30 | 230 | 0.15 | 0.03 | 0.0020 | 3.7 |
| 6. | 0.15 | 200 | 0.15 | 0.021 | 0.0022 | 3.3 |
| 7. | 0.15 | 215 | 0.16 | 0.024 | 0.0031 | 2.5 |
| 8. | 0.15 | 215 | 0.14 | 0.030 | 0.0032 | 2.8 |
| 9. | 0.18 | 250 | 0.18 | 0.020 | 0.0022 | 3.4 |
| 10. | 0.20 | 250 | 0.21 | 0.018 | 0.0025 | 2.7 |
| 11. | 0.19 | 200 | 0.14 | — | 0.0027 | 2.9 |
| 12. | 0.19 | 200 | 0.16 | — | 0.0028 | 2.8 |
| 13. | — | 200 | 0.20 | — | 0.0017 | 3.9 |
| 14. | — | 194 | — | — | 0.0041 | 2.1 |
| 15. | 0.20 | 204 | 0.15 | — | 0.0030 | 2.8 |

Example 16

Air-laid absorbent structures were formed using an air-forming machine, having a 1 meter wide line and three forming heads, available from Dan-Webb Forming, Risskov, Denmark. The formed absorbent structures had a basis weight of about 250 grams per square meter and consisted of about 95 weight percent southern softwood kraft pulp 6. The absorbent structure of claim 5 wherein the wettable cellulosic fibers exhibit a Wet Curl value that is between about 0.13 to about 0.22.

7. The absorbent structure of claim 6 wherein the wettable cellulosic fibers exhibit a Wet Curl value that is between about 0.15 to about 0.20.

8. The absorbent structure of claim 1 wherein the absorbent structure exhibits a Vertical Liquid Flux rate value at a height of about 15 centimeters of at least about 0.0025 grams of liquid per minute per gram per square meter of absorbent structure per inch of cross-sectional width of the absorbent structure.

9. The absorbent structure of claim 8 wherein the absorbent structure exhibits a Vertical Liquid Flux rate value at a height of about 15 centimeters of at least about 0.003 grams of liquid per minute per gram per square meter of absorbent structure per inch of cross-sectional width of the absorbent structure.

10. The absorbent structure of claim 1 wherein the absorbent structure exhibits a Vertical Liquid Flux rate value at a height of about 5 centimeters of at least about 0.01 grams of liquid per minute per gram per square meter of absorbent structure per inch of cross-sectional width of the absorbent structure.

11. The absorbent structure of claim 10 wherein the absorbent structure exhibits a Vertical Liquid Flux rate value at a height of about 5 centimeters of at least about 0.015 grams of liquid per minute per gram per square meter of absorbent structure per inch of cross-sectional width of the absorbent structure.

12. The absorbent structure of claim 1 wherein the absorbent structure exhibits a Wicking Time value of less than about 3.5 minutes.

13. The absorbent structure of claim 12 wherein the absorbent structure exhibits a Wicking Time value of less than about 3 minutes.

14. The absorbent structure of claim 1 wherein the absorbent structure, having a basis weight of about 200 grams per square meter, exhibits a dry tensile strength that is at least about 5000 grams of force per inch of absorbent structure width.

15. The absorbent structure of claim 14 wherein the absorbent structure, having a basis weight of about 200 grams per square meter, exhibits a dry tensile strength that is at least about 7500 grams of force per inch of absorbent structure width.

16. The absorbent structure of claim 1 wherein the absorbent structure, having a basis weight of about 200 grams per square meter, exhibits a wet tensile strength that is at least about 500 grams of force per inch of absorbent structure width.

17. The absorbent structure of claim 16 wherein the absorbent structure, having a basis weight of about 200 grams per square meter, exhibits a wet tensile strength that is at least about 1000 grams of force per inch of absorbent structure width.

18. The absorbent structure of claim 1 wherein the absorbent structure is prepared by a wet-laying process.

19. The absorbent structure of claim 1 wherein the absorbent structure is prepared by an air-laying process.

20. The absorbent structure of claim 19 wherein the absorbent structure comprises wettable cellulosic fiber s and binder fibers.

21. The absorbent structure of claim 1 wherein the fibers exhibit a Wet Curl value that is between about 0.11 to about 0.25, the absorbent structure exhibits a Vertical Liquid Flux rate value at a height of about 5 centimeters of at least about 0.01 grams of liquid per minute per gram per square meter of absorbent structure per inch of cross-sectional width of the absorbent structure, the absorbent structure exhibits a Wicking Time value of less than about 3.5 minutes, and the absorbent structure, having a basis weight of about 200 grams per square meter, exhibits a dry tensile strength that is at least about 5000 grams of force per inch of absorbent structure width and a wet tensile strength that is at least about 500 grams of force per inch of absorbent structure width.

22. The absorbent structure of claim 1 wherein the fibers are present in the absorbent structure in an amount of from about 50 to about 100 weight percent, based on the total weight of the absorbent structure.

23. The absorbent structure of claim 1 wherein the fibers are synthetic fibers.

24. The absorbent structure of claim 1 wherein the absorbent structure exhibits a density that is between about 0.08 to about 0.5 grams per cubic centimeter.

25. The absorbent structure of claim 1 wherein the absorbent structure exhibits a permeability between about 50 to about 1000 Darcys.

26. A disposable absorbent product comprising a liquid-permeable topsheet, a backsheet attached to the topsheet, and an absorbent structure positioned between the topsheet and the backsheet, wherein the absorbent structure comprises wettable cellulosic fibers, wherein the wettable cellulosic fibers exhibit a Wet Curl value that is between about 0.11 to about 0.25, and exhibits a Vertical Liquid Flux rate value at a height of about 15 centimeters of at least about 0.002 grams of liquid per minute per gram per square meter of absorbent structure per inch of cross-sectional width of the absorbent structure.

* * * * *

UNITED STATES PATENT AND TRADEMARK OFFICE
CERTIFICATE OF CORRECTION

PATENT NO. : 5,843,852
DATED : December 1, 1998
INVENTOR(S) : Jacek Dutkiewicz et al.

Page 1 of 1

It is certified that error appears in the above-identified patent and that said Letters Patent is hereby corrected as shown below:

Column 1,
After the Title at lines 1-2, and before Background of The Invention, insert:

This application claims priority from U.S. Provisional Application No. 60/008,994 filed on December 21, 1995.

Signed and Sealed this

Second Day of October, 2001

Attest:

*Nicholas P. Godici*

NICHOLAS P. GODICI
*Attesting Officer*   *Acting Director of the United States Patent and Trademark Office*